US005769083A

United States Patent [19]
MacEachern

[11] Patent Number: 5,769,083
[45] Date of Patent: Jun. 23, 1998

[54] PRESSURE TRANSDUCER POSITIONING SYSTEM

[75] Inventor: A. Walter MacEachern, Woburn, Mass.

[73] Assignee: Gatron Corporation, Woburn, Mass.

[21] Appl. No.: 612,338

[22] Filed: Mar. 6, 1996

Related U.S. Application Data

[63] Continuation-in-part of Ser. No. 198,838, Feb. 18, 1994.

[51] Int. Cl.[6] ........................................................ A61B 5/02
[52] U.S. Cl. ............................................................. 128/673
[58] Field of Search ................................... 128/672–675; 33/379; 312/223.5

[56] References Cited

U.S. PATENT DOCUMENTS

| | | | |
|---|---|---|---|
| 3,495,585 | 2/1970 | Halligan et al. | 128/2.05 |
| 3,590,818 | 7/1971 | Lemole | 128/214 |
| 3,693,612 | 9/1972 | Donahoe et al. | 128/2.05 |
| 4,539,998 | 9/1985 | McCord et al. | 128/675 |
| 4,545,389 | 10/1985 | Schaberg et al. | 128/748 |
| 4,557,269 | 12/1985 | Reynolds et al. | 128/675 |
| 4,576,181 | 3/1986 | Wallace et al. | 128/675 |
| 4,589,287 | 5/1986 | Dickens | 73/727 |
| 4,638,811 | 1/1987 | Bisera et al. | 128/673 |
| 4,669,484 | 6/1987 | Masters | 128/673 |
| 4,679,567 | 7/1987 | Hanlon et al. | 128/675 |
| 4,691,710 | 9/1987 | Dickens | 128/672 |
| 4,776,343 | 10/1988 | Hubbard et al. | 128/675 |
| 4,779,626 | 10/1988 | Peel et al. | 128/675 |
| 5,168,633 | 12/1992 | Harrison et al. | 33/512 |
| 5,280,789 | 1/1994 | Potts | 128/672 X |

Primary Examiner—Francis Jaworski
Attorney, Agent, or Firm—Hamilton, Brook, Smith & Reynolds, P.C.

[57] ABSTRACT

An optical system for positioning a pressure transducer relative to a patient to provide for accurate measurement of bodily fluids within the patient. A light source such as a laser is used to direct light onto a specified location on the human body to accurately identify the elevation of the transducer relative to the specified location to provide an absolute measurement of fluid pressure.

20 Claims, 6 Drawing Sheets

PRESSURE TRANSDUCER POSITIONING SYSTEM

RELATED APPLICATIONS

This is a Continuation-in-Part application of U.S. application Ser. No. 08/198,838 filed on Feb. 18, 1994 incorporated herein by reference.

BACKGROUND OF THE INVENTION

During medical procedures as well as pre and post operation conditions, monitoring of fluid pressure within the patient is necessary in conjunction with the assessment of the patient care and treatment. The fluid pressure monitoring is most commonly arterial blood pressure, but knowledge concerning intracranial fluid pressure, venous pressure, and intraheart pressure also can provide important insight into a patient's current condition. One of the most effective devices for these types of measurements is a pressure transducer directly communicating with the particular bodily fluid of interest. Typically, the patient is catheterized and a tube, usually containing saline fluid pressure, provides a fluid communication path between the bodily fluid and the pressure transducer. Then, the electrical impulses generated by the pressure transducer, which are a function of the bodily fluid pressure, are displayed by a monitor or other display device to monitor specific body functions.

The transducer housing is usually mounted in close proximity to the patient on an I.V. pole with the I.V. bag providing the saline solution. If the user desires only information regarding the dynamics of the bodily fluid pressure, then the pressure transducer can be mounted virtually anywhere vertically on the I.V. pole. If the user, however, desires to monitor the absolute pressure of the bodily fluid, then the pressure transducer must be mounted in a fixed relationship to the patient. For example, if arterial pressure is to be monitored, then the pressure transducer must be mounted approximately at the level of the heart.

A continuing need exists to provide accurate reproducible methods for monitoring hemodynamic pressure. Variations in the position of the sensor system relative to the patient continue to result in improper assessment of the patients condition which may adversely effect decisions regarding the course of treatment including selection of medications administered to adjust fluid pressure.

SUMMARY OF THE INVENTION

The present invention relates to a mounting assembly on which pressure transducers can be mounted and used to accurately measure blood pressure within human or animal bodies. A preferred embodiment utilizes a light source on the mounting assembly that emits light that is directed by the user at an object to accurately position pressure transducers that are positioned in a fixed relationship relative to the light source. As the transducers are, for many applications, aligned with a horizontal plane extending through the middle of the patient's heart, the light source can be directed by the user at the patient's heart to provide the necessary alignment.

Currently, the user simply aligns the transducer with the patient's body using his or her eye. However for a large number of patients and operating and operating conditions, for every inch of misplacement of the transducer relative to the mid-heart plane, there is a difference in measured pressure in the range of 2–9 mm of mercury. The present invention is used to prevent the inaccuracies associated with this procedure to provide a more dependable and reproducible measurement of arterial or fluid pressure.

A preferred embodiment of the invention uses a light weight battery powered laser mounted on a molded plastic assembly as a light source. The plastic assembly is mountable on a standard IV pole and has a number of receiving members or connectors on which disposable pressure transducers are mounted.

The system can use a photodetector or light sensor to sense whether the beam of light emitted by the laser is directed at the desired location. The sensor can be positioned on the patient by the user and is connected by wire or wireless remote to an alarm or indicator circuit mounted on the frame that houses the laser. The sensor can also be mounted on the frame and used with a reflector located on the patient. An audible alarm or light indicator mounted on the frame can be used to signal the user that the patient or the transducer has moved out of position and requiring realignment of the patient relative to the transducer.

A circuit controlling operation of the laser can include switches to provide for continuous, periodically pulsed or manual operation of the light source.

Manually operated knobs can be incorporated into the mounting frame to level the frame relative to a horizontal plane. Standard levelors can be included in the frame so that the user can usually verify that the frame is level.

In another preferred embodiment of the invention a module can be attached to the rear of the transducer mounting plate. This module can be used to mount the transducer assembly to the I.V. pole and can house the light circuit and other circuit components. This system can be used with all available transducer systems, is inexpensive and does not interfere with standard operation of multi-transducer systems.

The above and other features of the invention including various novel details of construction and combinations of parts will now be more particularly described with reference to the accompanying drawings and pointed out in the claims. It will be understood that the particular transducer mounting plate embodying the invention is shown by way of illustration and not as a limitation of the invention. The principles and features of this invention may be employed and varied in numerous embodiments without departing from the scope of the invention.

DETAILED DESCRIPTION OF THE INVENTION

Figure 1:
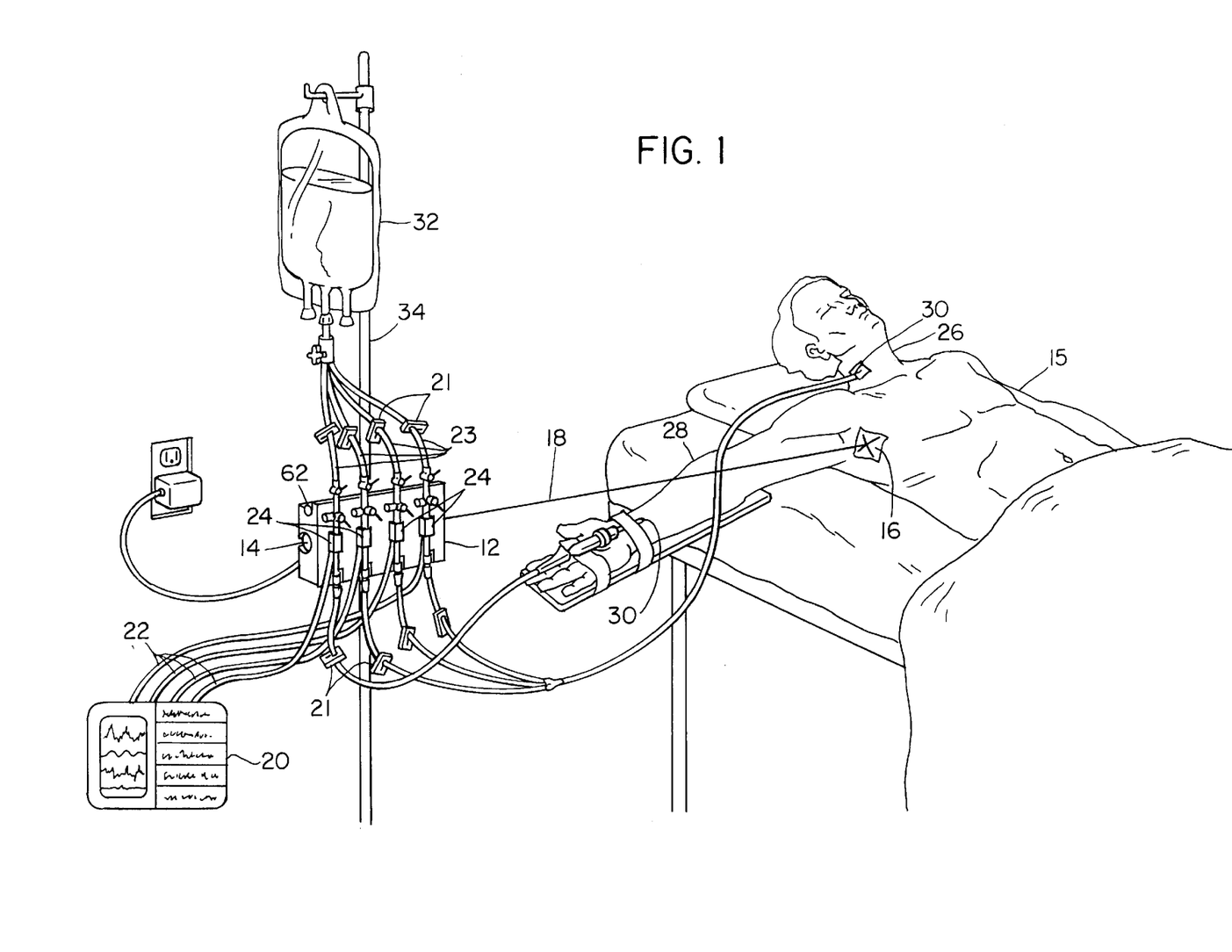
FIG. 1 is a schematic view of the pressure transducer and associated devices in relation to the patient.

Turning now to the drawings, FIG. 1 is the general configuration for monitoring blood pressure of a patient 15 using one or more pressure transducers. Here, an I.V. bag 32 containing saline solution is hung from an I.V. pole 34. The flow of the saline solution is provided through the transducers 24 to the patient via the saline tube. On this tube, a fluid flow restricter and flusher are placed so that the flow level can be controlled and the system flushed out. Also in line, between the patient and the I.V. bag, each transducer 24 is positioned connecting a first saline tube, I.V. side, to a second saline tube, on the patient side of the transducer. Each transducer 24 is electrically connected to a blood pressure monitor 20 via a connecting wire 22 so that the pressure monitored by each transducer can be displayed to the user.

A transducer, configured as described above, is capable of monitoring blood pressure based upon the principle that the pressure of the saline solution in the saline tube, patient side, fluctuates as a function of the blood pressure at the vascular position in which the catheter 30 is lodged. More specifically, the hemodynamic pressures generated by the pumping action of the heart are transmitted through the blood within the patient's body, through the catheter 30, and into the saline tube. A light source 14, such as a laser, is used to generate a beam of light directed along an optical path 18 to a desired location 16 on the patient 15. Catheters 30 are inserted at various locations including the neck 26 or arm 28 to monitor different locations.

Figure 2:
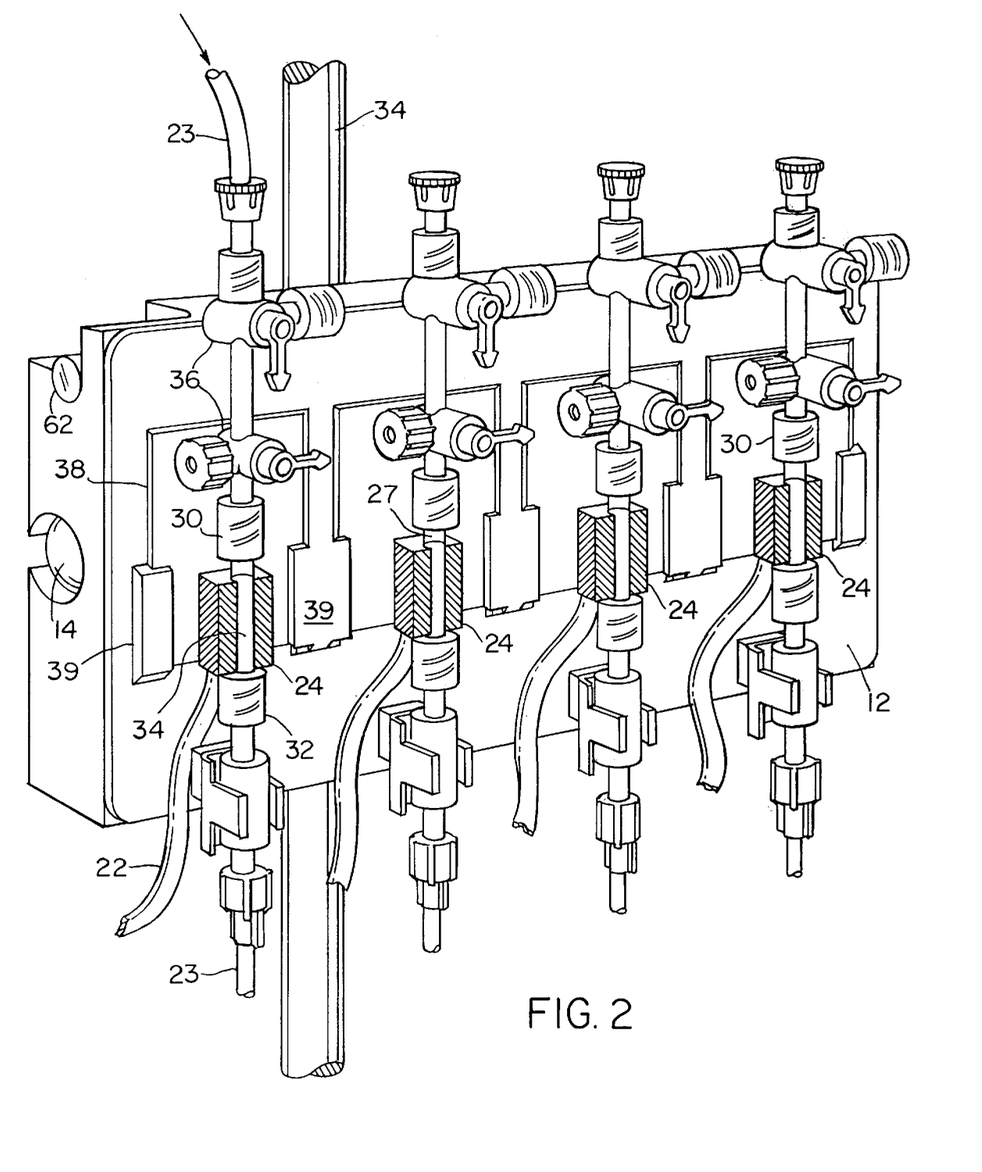
FIG. 2 is a perspective view of four typical pressure transducers on mounting plate or frame.

Turning now to FIG. 2, a more detailed perspective view of the transducer housing and support plate is illustrated. The support plate 12 is provided with mechanical connections capable of being connected to the I.V. pole 34. A level indication 25 is provided on this support plate 12 to indicate the proper level of the transducers 24 in relation to the mid-level of the patient heart. The transducer housing comprises a fluid connection inlet port for connecting to the saline tube, I.V. bag side. A fluid connection outlet port then connects to the saline tube, patient side. Connecting the inlet and outlet ports is a duct housed within each transducer housing. The saline solution within this duct has a pressure which pulsates in response to the blood pressure. Each transducer is housed in fluid communi-cation with this duct, and moves a plate across an electrical assembly which generates an electrical signal that is a function of the pressure of the saline solution. A number of commercially available transducers can be used with the present invention.

The transducer also has a flow valve connected to it for controlling the flow of saline solution through the duct. That is, if there is blood backflow through the saline tube, patient side, then the flow valve can be actuated by the user to purge the duct and the saline tubes of blood. The transducer housing is supported on a plastic tubing 27 which has a pair of slots corresponding to the notched flanges of the support plate so that the transducer base can be mounted on the support plate by aligning the flanges with the slots and then sliding the transducer base in a downward direction or by snapping it into an aperture in the plate. Finally, an electrical socket provides an electrical connection to the blood pressure monitor so that the electrical power is supplied to the transducer and impulses generated by transducer can be transmitted to the monitor.

As explained above, the support plate has a level indication which is aligned with the level of the patient's heart so that the transducer can obtain an accurate absolute measurement of the pressure within the carotid artery. Typically in operation, the user must lower his head to the level of the level indication and then visually align it with a region on the patient's side that corresponds to the approximate mid-level of the heart. This mode of operation presents a number of problems. First, in the close quarters of the usual operating room, many times there is insufficient space next to the I.V. pole for the user to perform visual alignment. Moreover, even if this can be performed, the visual alignment technique is subject to inaccuracies arising out of improper lining up of the level indication which may be four feet or more from the patient. Finally, if the support plate should become jarred or misaligned during operation or if the patient is moved, there is no way to confirm its proper alignment from the standing position or from the other side of the patient.

Figure 3:
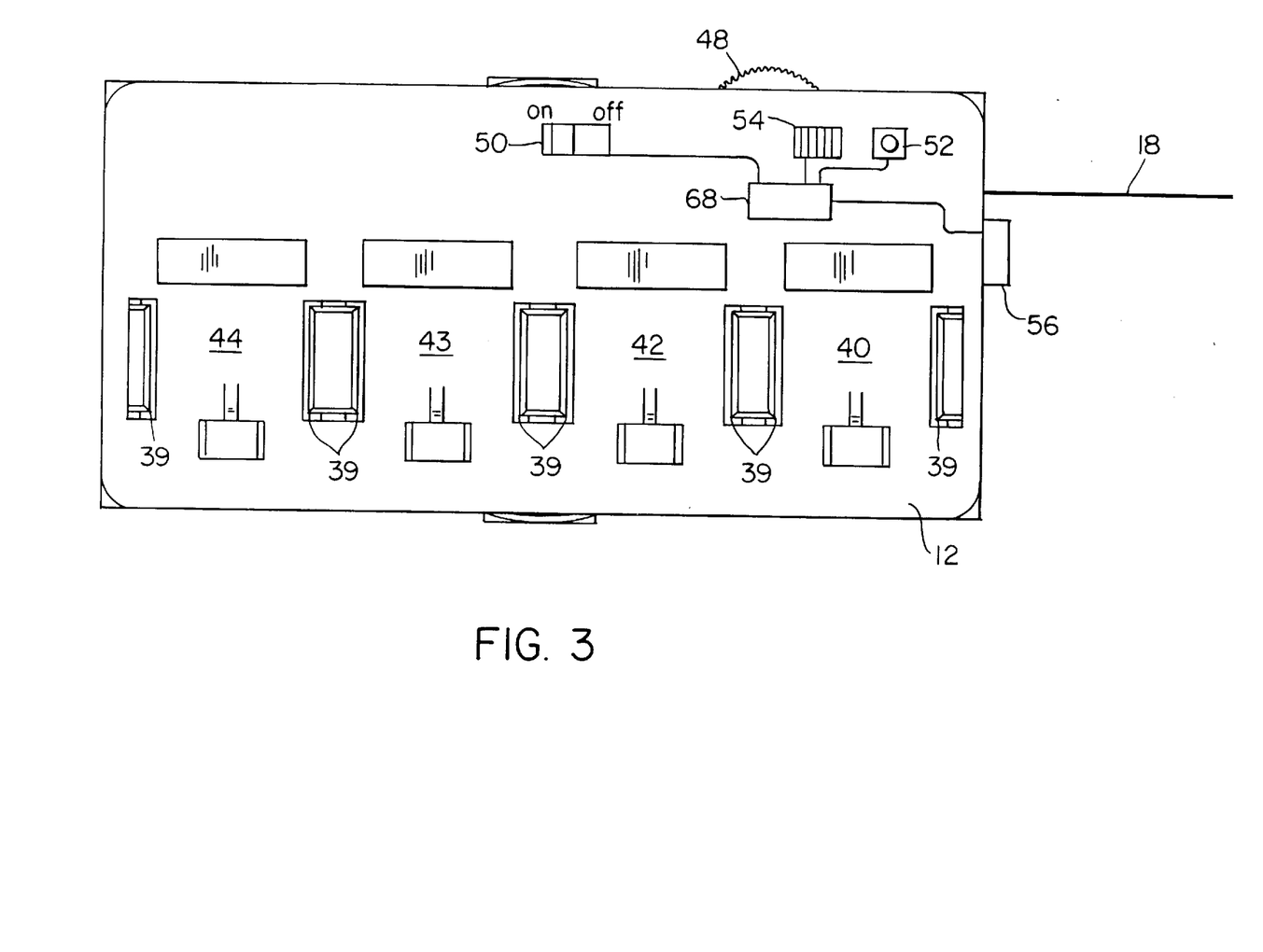
FIG. 3 is a front view of the transducer mounting plate of the present invention.

FIG. 3 is a front view of the transducer mounting plate 12 constructed according to the principles of the present invention. More specifically, the front of the transducer plate is provided with four regions 40, 42, 43, 44 for mounting four different pressure transducers by adhesive, the flange and slot technique described above or other suitable means. Each one of the four corresponding transducers is connected to monitor blood pressure from a different point in the patient. The plate or frame 12 can include a light indicator 52 or audible alarm 54 connected to a sensor 56 if the sensor detects misalignment of the optical path with the desired location 16. The sensor can measure light returning from a reflector positioned at 16. Alternatively the sensor can be positioned at the location 16. A switch 50 can select continuous, intermittent or manual operation of the light source and the circuit 68 within the housing. A manual knob 48 can be used to level the plate 12 relative to the horizontal plane.

Figure 4:
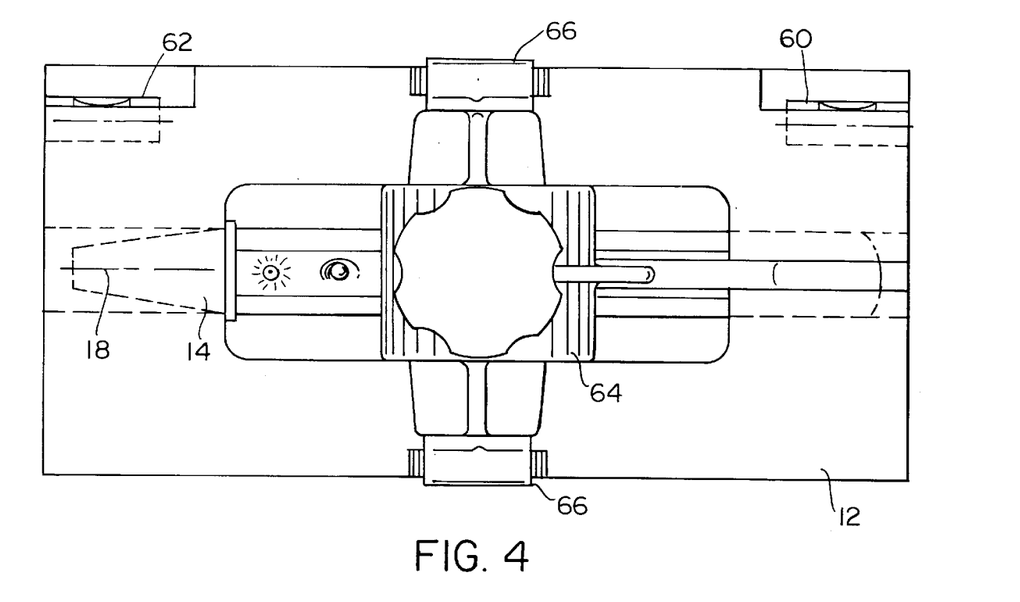
FIG. 4 is a rear view of the mounting plate.

FIG. 4 is a rear view of the transducer mounting plate 12. Here, two liquid tube levels 60, 62 are provided at opposite lateral ends of the plate so that the plate, and consequently the transducers themselves, can be leveled from a standing position. Further, a 0.5–5 mW laser pointer 14 generates a collimated beam of light parallel to the level line of the level tubes along optical path 18. Mounting bracket 64 connects the plate 12 to the I.V. pole.

Figure 5:
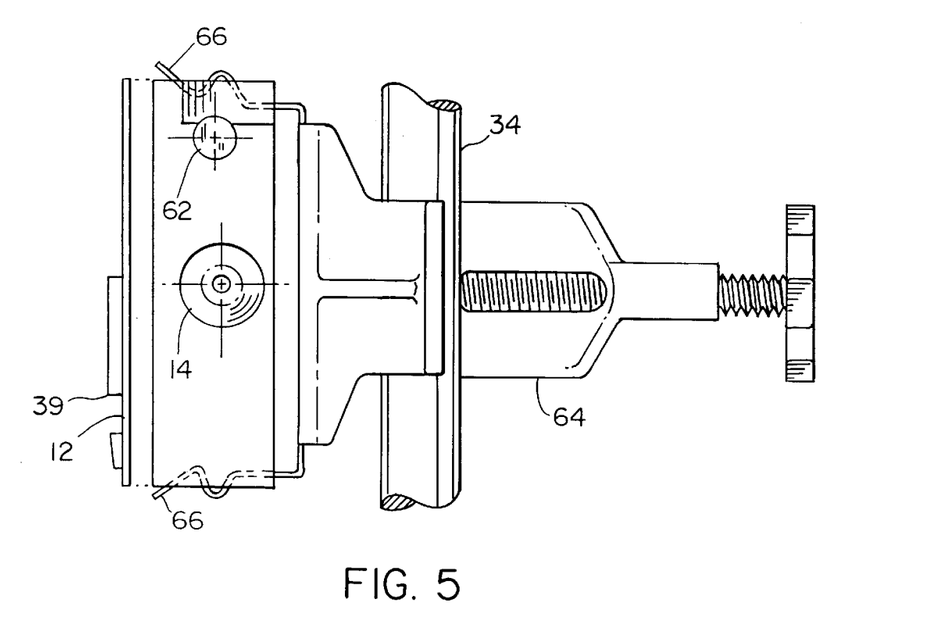
FIG. 5 is a side cross-sectional view of the mounting plate.

Finally, FIG. 5 illustrates a cross-sectional side view showing the laser pointer disposed below the liquid level tubes. Projecting from the front plate are transducer manifolds for communicating with slots formed in the transducer bases to support the transducers. Extending from the rear of the transducer plate, an I.V. pole clamp is attachable to an I.V. pole.

In operation of the present invention, the transducer plate is first leveled using the level tubes. This can be easily accomplished from the standing position while rotating the transducer plate. Once the transducer plate has been leveled, then its vertical location relative to the patient's heart can be determined by viewing the point of light generated by the laser on the patient's side. When this point of light is shining on the patient's side at the vertical position of the patient's heart, then the transducers of the transducer plate are properly positioned. As a result, not only can the alignment of the transducers be performed without squatting next to the I.V. pole, but the proper alignment of the transducer plate can be quickly confirmed during operation by simply inspecting the status of the level tubes and then the position of the light spot of the patient's side.

The transducers 24 are used to measure standard arterial pressure, pulmonary artery pressure, occluded pulmonary pressure, right atrial/central venous pressure, and left atrial/ pressure, for example. These measurements are commonly used to diagnosis the patient's condition and determine what medications and how much of these should be administered to the patient. The user can inject medications directly into the lines used to monitor fluid pressure in many applications.

Another preferred embodiment of the present invention can be used in conjunction with existing mounting plate assemblies without interfering with their current methods of monitoring fluid pressure. In this embodiment the light source, level, and clamp are included in a single assembly that attaches to the back of existing transducer mounting plates. In this way, the system does not interfere with set up and use of the pressure monitoring system, does not require alterations to be made to the system, can be balanced prior to installation to minimize the risk of angular misalignment, is rigidly aligned in the vertical direction relative to the transducers thereby avoiding possible vertical misalignment by the user, and is readily accessible by the user.

Figure 6:
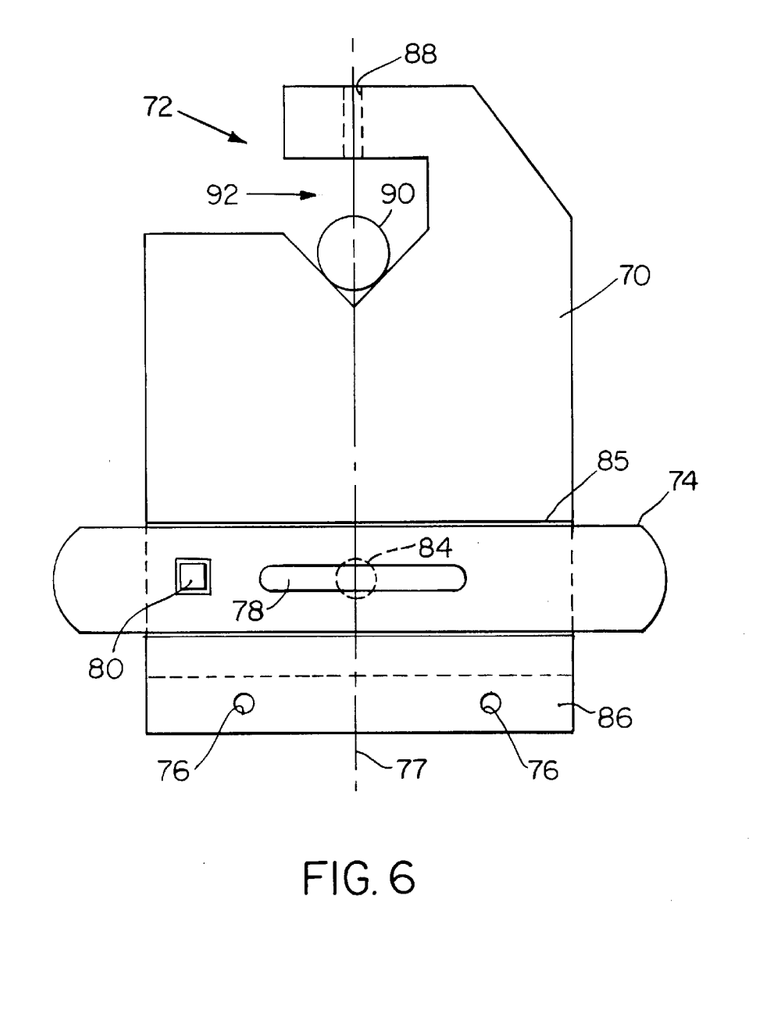
FIG. 6 is a top view of a rear mounting module in accordance with the invention.
Figure 7:
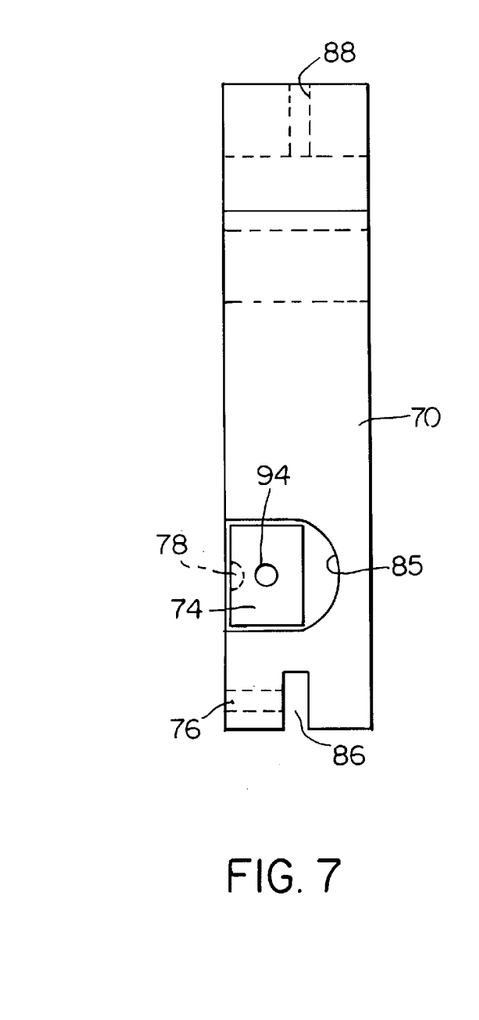
FIG. 7 is a side view of thy module depicted in FIG. 6
Figure 8:
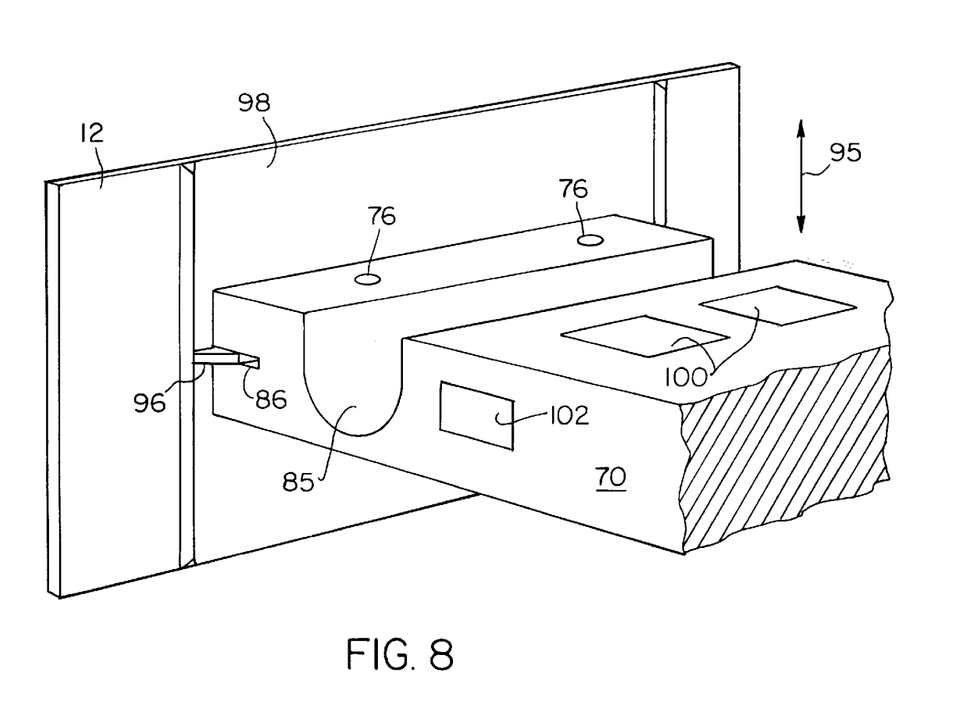
FIG. 8 is a rear partial perspective view of a mounting plate connected to the module shown in FIG. 6.

The rear mounted module is illustrated in FIG. 6-8. In FIG. 6, the support module 70 can be attached to the rear 98 of the mounting plate 12. The module includes a cavity 85 in which a light source such as a laser 94 is mounted. The cavity can also retain a housing in which the laser 94, a level 78, a lamp 84 that illuminates the level 78, and a switch 80 having "on" and "off" positions, are configured. Both the lamp 84 and the laser 94 are actuated by the switch 80. Holes 76 extending through one end of the module 70 are used to attach the module to the rear of the mounting plate 12. The plate 12 has a rib 96 extending horizontally which can mate with slot 86 in the module 70. At the opposite end of the module 70 is a holder 72 including a threaded hole 88 used to secure the module 70 to an I.V. pole 90 or other mechanism used to vertically position plate 12. The holder 72 has an opening 92 on one side through which the pole 90 is inserted.

By hand adjustment of a bolt the user can move the plate 12 and the module 70 in the vertical direction along pole 90 so that the mounting plate 70 and transducers can be translated relative to the patient. In another embodiment, a second finer adjustment can also be made along the vertical axis 95 with another mechanical actuator that can be incorporated into the module 70. The components of the module are positioned relative to center axis 77 to provide the desired balance to the system by locating the center of gravity of the module, as well as the plate 12 and transducer system, along the axis 77. This minimizes any torque on the mounting plate and helps to keep the mounting plate level during use.

The module can be a molded or machined plastic material. The laser, level and switch can be mounted in a single cavity 85 or attached to the module 70 in separate cavities 100 or mounting positions. As shown in the side view of FIG. 7, the laser 94 is directed along an output path from one longitudinal end of a light source housing 74. The housing 74 can include the level 78, the switch 80 and the lamp 84, as well as the laser 94. There can also be a plurality of levels attached to the module 70 in another embodiment. Holes 76 can be threaded so that bolts or thumb screws can be used to secure module 70 to the rear side 98 of plate 12. Plate 12 typically has several ribs on the rear side to strengthen the plate. The module 70 can be shaped to attach to any of these ribs. In FIG. 8, a horizontal rib 96 on plate 12 slides into the horizontal slot 86 in module 70.

The audible and/or visual alarm described previously to alert the user that the patient is no longer positioned properly relative to the transducer assembly, or that the assembly is no longer level, can be mounted on the module 70. The alarm can consist of a warning light that goes on (or off) when the unwanted condition occurs.

The module 70 can be powered by a battery within the housing 74, a battery in the module 70, along with a circuit connecting the components, or connector 102 can be used to electrically connect the module 70 or housing 74 to an outlet or other external source.

EQUIVALENTS

Those skilled in the art will know or be able to ascertain using no more than routine experimentation, many equivalents to the specific embodiments of the invention described herein.

These and all other equivalents are intended to be encompassed by the following claims.

I claim:

1. An optical positioning system for a bodily fluid pressure transducer comprising:

a mounting plate having a first side on which a pressure transducer is mounted and a second side, the pressure transducer measuring fluid pressure in a patient;

a support assembly attached to the second side of the mounting plate, the support assembly having an adjustable holder such that the mounting plate and support assembly can be vertically translated by a user; and a light source mounted between the second side of the mounting plate and the holder, the light source emitting light such that the user can vertically alter the relative position between the pressure transducer and the patient.

2. The optical positioning system of claim 1 wherein the mounting plate further comprises a plurality of connectors spaced along a lateral axis of the mounting plate.

3. The optical positioning system of claim 1 wherein the light source further comprises a light source housing attached to the second side of the mounting plate.

4. The optical positioning system of claim 3 wherein the light source housing mounted to a rib on the second side of the mounting plate.

5. The optical positioning system of claim 4 wherein the light source comprises a laser light source and further comprising a level and a switch that actuates the laser light source.

6. The optical positioning system of claim 1 further comprising a light source housing positioned within a cavity of the support assembly, the light source being positioned within the light source housing.

7. The optical positioning system of claim 1 wherein the light source comprises a laser light source and further comprising a level and a switch that actuates the laser light source.

8. The optical positioning system of claim 1 further comprising a light indicator that indicates misalignment of the pressure transducer relative to the patient.

9. An optical positioning system for a bodily fluid pressure transducer comprising:

a mounting plate having a first side on which a pressure transducer is mounted and a second side, the pressure transducer measuring fluid pressure in a patient;

a support assembly attached to the second side of the mounting plate, the support assembly having an adjustable holder such that the mounting plate and support assembly can be vertically translated by a user; and a light source mounted on the support assembly, the light source emitting light such that the user can vertically position the pressure transducer relative to the patient.

10. The optical positioning system of claim 9 wherein the mounting plate further comprises a plurality of connectors spaced along a lateral axis of the mounting plate.

11. The optical positioning system of claim 9 wherein the light source further comprises a light source housing attached a cavity in the support assembly.

12. The optical positioning system of claim 9 further comprising a light source housing positioned within a cavity of the support assembly and a switch within the housing to actuate the light source that is mounted to the light source housing.

13. The optical positioning system of claim 9 further comprising a lamp that illuminates a level on the mounting plate or the support assembly.

14. A method for optically positioning a bodily fluid pressure transducer comprising:

providing a mounting plate having a first side on which a pressure transducer is mounted and a second side, the pressure transducer measuring fluid pressure in a patient;

attaching a support assembly to the second side of the mounting plate, the support assembly having an adjustable holder such that the mounting plate and support assembly can be vertically translated by a user; and directing light from a light source mounted between the second side of the mounting plate and the holder onto a patient such that the user can vertically alter the relative position between the pressure transducer and the patient.

15. The method of claim 14 further comprising providing a plurality of transducer connectors spaced along a lateral axis of the mounting plate.

16. The method of claim 14 further comprising providing a light source housing attached to the second side of the mounting plate, the light source being mounted to the light source housing.

17. The method of claim 14 further comprising positioning a light source housing within a cavity of the support assembly, the light source being mounted to the light source housing.

18. The method of claim 14 wherein the light source comprises a laser light source and further comprises a level and a switch that actuates the laser light source.

19. The method of claim 14 further comprising balancing the support assembly along a mounting plate axis.

20. The method of claim 14 further comprising illuminating the level with a light.

* * * * *